US010213538B2

United States Patent
Rudser

(10) Patent No.: US 10,213,538 B2
(45) Date of Patent: Feb. 26, 2019

(54) IMPLANTED DEVICE WITH WIRELESS ENERGY TRANSFER AND EXTERNAL ALIGNMENT FEATURE

(71) Applicant: HeartWare, Inc., Miami Lakes, FL (US)

(72) Inventor: John Rudser, Miami, FL (US)

(73) Assignee: HeartWare, Inc., Miami Lakes, FL (US)

(*) Notice: Subject to any disclaimer, the term of this patent is extended or adjusted under 35 U.S.C. 154(b) by 0 days.

(21) Appl. No.: 14/857,130

(22) Filed: Sep. 17, 2015

(65) Prior Publication Data

US 2016/0082171 A1 Mar. 24, 2016

Related U.S. Application Data

(60) Provisional application No. 62/052,163, filed on Sep. 18, 2014.

(51) Int. Cl.
*A61M 1/10* (2006.01)
*A61M 1/12* (2006.01)
(Continued)

(52) U.S. Cl.
CPC .......... *A61M 1/127* (2013.01); *H02J 7/0042* (2013.01); *H02J 7/025* (2013.01); *A61M 1/101* (2013.01);
(Continued)

(58) Field of Classification Search
CPC . A61N 1/3787; A61N 1/37229; A61B 5/0215
See application file for complete search history.

(56) References Cited

U.S. PATENT DOCUMENTS 5,591,217 A * 1/1997 Barreras ............ A61N 1/37223
607/61
5,833,655 A * 11/1998 Freed ................ A61M 39/0247
604/174
(Continued)

FOREIGN PATENT DOCUMENTS

EP 0241307 A2 10/1987
JP 62-246378 A 10/1987
(Continued)

OTHER PUBLICATIONS

International Search Report and Written Opinion for Appln. No. PCT/US2015/050727 dated Nov. 27, 2015.
(Continued)

*Primary Examiner* — Michael D Abreu
(74) *Attorney, Agent, or Firm* — Christopher & Weisberg, P.A.

(57) ABSTRACT

An implant device includes a housing and an energy receiving element disposed in the housing. The energy receiving element is configured to be electrically connected to an energy-consuming device. The implant device is configured to be mounted within a body of a human or non-human animal. The housing includes a feature configured to be accessible through skin of the animal and to receive a corresponding mating member of an external charger including an energy transmitting element. The energy receiving element is configured to receive energy wirelessly from the energy transmitting element when the external charger is mated with the housing.

18 Claims, 1 Drawing Sheet

(51) Int. Cl.
*H02J 7/02* (2016.01)
*H02J 7/00* (2006.01)
*A61N 1/378* (2006.01)

(52) U.S. Cl.
CPC ..... *A61M 1/122* (2014.02); *A61M 2205/3523* (2013.01); *A61N 1/3787* (2013.01)

(56) References Cited

U.S. PATENT DOCUMENTS

| | | | | |
|---|---|---|---|---|
| 5,861,018 A | * | 1/1999 | Feierbach | A61B 5/0028 |
| | | | | 128/899 |
| 6,024,704 A | * | 2/2000 | Meador | A61B 5/0215 |
| | | | | 128/899 |
| 6,478,820 B1 | | 11/2002 | Weiss | |

FOREIGN PATENT DOCUMENTS

| | | |
|---|---|---|
| JP | 9-508553 A | 9/1997 |
| WO | 2005065738 A2 | 7/2005 |
| WO | 2007126454 A2 | 11/2007 |

OTHER PUBLICATIONS

Japanese Office Action for Application No. 2017-514804, dated Mar. 20, 2018.

\* cited by examiner

IMPLANTED DEVICE WITH WIRELESS ENERGY TRANSFER AND EXTERNAL ALIGNMENT FEATURE

CROSS REFERENCE TO RELATED APPLICATIONS

The present application claims the benefit of the filing date of U.S. Provisional Application No. 62/052,163, filed Sep. 18, 2014, entitled Implanted Device With Wireless Energy Transfer and External Alignment Feature, the disclosure of which is hereby incorporated herein by reference.

FIELD OF INVENTION

The present invention relates to an implanted device with wireless energy transfer.

BACKGROUND OF THE INVENTION

It is often necessary to provide an implanted medical device to assist an organ of a human or a non-human animal or as a substitute for the organ. Examples of such implanted device include a ventricular assist device (VAD) implanted in a patient's body to take over some or all of the pumping function of the heart as well as other cardiac assist devices and artificial heart pumps. While the devices are implanted within a patient's body, such devices may be supplied energy from an implanted or an external power source. Implanted power sources generally have limited power capacity due to constraints, such as size and weight. Thus, the internal power sources may need to be augmented or recharged continuously or at frequent intervals. A conventional manner for supplying intermittent or continuous power to the implanted device is to use a pair of induction coils. A secondary or receiving coil is implanted within the body. A primary or charging coil may be aligned externally with the receiving coil for transcutaneous energy transfer (TET).

TET involves power transfer across the skin without direct electrical connectivity. Because the electrical power is transmitted through the skin, the amount of power transmitted may be limited to avoid damaging the skin. Efficient transfer of power between the primary coil and the secondary coil requires proper orientation and alignment therebetween, which may be difficult to obtain because the secondary coil is implanted under the skin. The embodiments described below may alleviate one or more of these drawbacks.

BRIEF SUMMARY OF THE INVENTION

An embodiment of the invention includes an implant device including a housing and an energy receiving element disposed in the housing. The energy receiving element is configured to be electrically connected to an energy-consuming device. The implant device is configured to be mounted within a body of an animal. The housing comprises a feature configured to be accessible through skin of the animal and to receive a corresponding mating member of an external charger comprising an energy transmitting element. The energy receiving element is configured to receive energy wirelessly from the energy transmitting element when the external charger is mated with the housing.

According to an aspect of the invention, a wireless energy transfer system comprises an implant device and an external charger. The implant device is configured to be at least partially mounted within a body of an animal. The implant device comprises a first housing and an energy receiving element disposed in the first housing. The energy receiving element is configured to be electrically connected to an energy-consuming device. The first housing comprises a feature configured to be accessible through skin of the animal. The external charger comprises a second housing and an energy transmitting element disposed in the second housing. The energy transmitting element is configured to be electrically connected to an energy source. The second housing comprises a mating member configured to mate with the feature of the first housing. When the first and second housings are mated to one another, the energy transmitting element is aligned to wirelessly transmit energy to the energy receiving element.

BRIEF DESCRIPTION OF THE DRAWINGS

Various embodiments of the present invention will now be discussed with reference to the appended drawings. It is to be appreciated that these drawings depict only some embodiments of the invention and are therefore not to be considered limiting of its scope.

DETAILED DESCRIPTION

Figure 1:
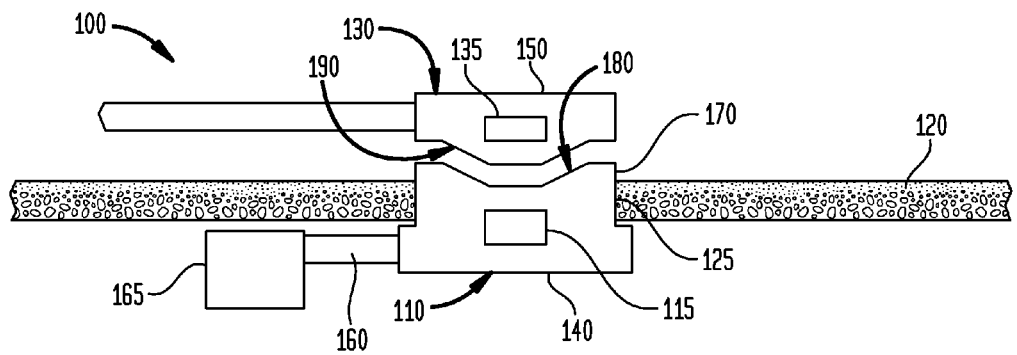
FIG. 1 is a schematic illustration of a wireless energy transfer system having an external alignment feature, according to an embodiment of the disclosure.

The following discussion describes, in detail, various aspects and embodiments of the present invention. This discussion should not be construed as limiting the invention to those particular aspects or embodiments. Rather, practitioners skilled in the art will recognize numerous other aspects and embodiments as well, which are within the scope of the present invention.

In describing the embodiments of the present invention illustrated in the drawings, specific terminology will be used for the sake of clarity. For purposes of explanation, the invention is generally described herein with regard to an implanted device. However, the present invention is not intended to be limited to the specific terms so selected.

Referring now to FIG. 1, a wireless energy transfer system 100 is illustrated schematically. The system 100 includes an implant device 110 implanted under skin 120 and an external charger 130. The implant device 110 includes an energy receiving element 115 disposed in a housing 140 and the external charger 130 includes an energy transmitting element 135 in a housing 150. In the illustrated embodiment, a lead 160 extends from the implant device 210 to an energy consuming device 165 implanted in an animal's body for supplying energy to the power-consuming device. In another embodiment, the energy consuming device 165 may also be disposed in the housing 140 of the implant device.

The implant device 110 is implanted under the skin 120 such that at least a part 170 of the housing 140 protrudes across the skin through an opening 125 in the skin. While in the illustrated embodiment, the part 170 protrudes across the skin 120, in other embodiments, the part of the housing may be generally flush with the skin and be accessible to an external charger. The protruding part 170 includes a feature 180 having a predetermined geometry. Likewise, the housing 150 has a mating member 190. The mating member 190 has a geometry complementary to the feature 180 such that the mating member mates with the feature of the protruding part 160 when urged against one another. In an exemplary configuration, the feature 180 takes the form of an indentation and the mating member 190 is correspondingly shaped to complement the indentation. Thus, the feature 180 aids in mechanical alignment of the housing 250 of the external charger 130 with the housing 140 of the implant device 110.

Figure 2:
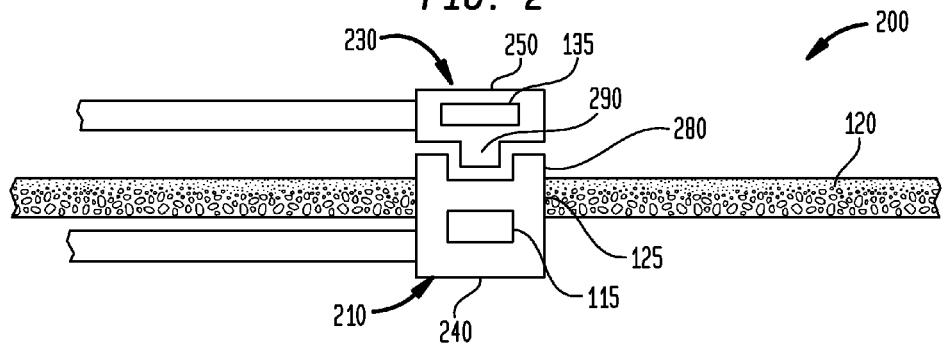
FIG. 2 is a schematic illustration of a wireless energy transfer system having an external alignment feature, according to another embodiment of the disclosure.

Referring now to FIG. 2, a wireless energy transfer system 200 is illustrated, according to another embodiment of the disclosure. The system 200 includes an implant device 210 implanted under the skin 120 and an external charger 230. The implant device 210 includes a housing 240 having a feature 280. The external charger 230 includes a housing 250 having a mating member 290. As illustrated in FIG. 2, the feature 280 of implant device 210 takes the form of a socket-like connector and the mating member 290 of the external charger 230 takes the form of a button configured to be securely accommodated by the socket-like connector. Thus, the feature 280 aids in mechanical alignment of the housing 250 of the external charger 230 with the housing 240 of the implant device 210.

Referring to both FIGS. 1 and 2, the implant devices 110, 210 include an energy receiving element 115 and the external chargers 130, 230 include an energy transmitting element 135. The energy transmitting element 135 is configured to transmit energy wirelessly and correspondingly the energy receiving element 115 is configured to receive energy wirelessly. In an exemplary embodiment, the energy transmitting element 135 takes the form of a primary coil of a transformer whereas the energy receiving element 115 takes the form of a secondary coil of the transformer. When the elements 115, 135 are aligned to one another, energy may be transferred from the wirelessly via induction, as is known in the art. The features 180, 280 and the mating members 190, 290 are so configured as to ensure proper alignment between the energy transmitting element 135 and the energy receiving element 115.

In another embodiment, the energy receiving element 215 may take the form of an RF antenna and the energy transmitting element 135 may take the form of an RF transmitter. Thus, energy transfer between the external chargers 130, 230 and the implant devices 110, 210 may be effectuated via RF transmission. In yet other embodiment, the energy receiving element 115 may take the form of an ultrasonic receiver whereas the energy transmitting element 135 may take the form of an ultrasonic transmitter. In this configuration the energy transfer between the external chargers 130, 230 and the implant devices 110, 210 may be achieved via ultrasonic transmission.

In still further embodiment, the energy receiving element 115 may take the form of an optical receiver whereas the energy transmitting element 135 may take the form of an optical transmitter, for example, a LASER or a light emitting diode for transferring energy via optical energy. It will thus be understood that many different modes of wireless energy may be employed for transferring energy from the external charger to the implant without departing from the scope of the instant disclosure.

Figure 3A:
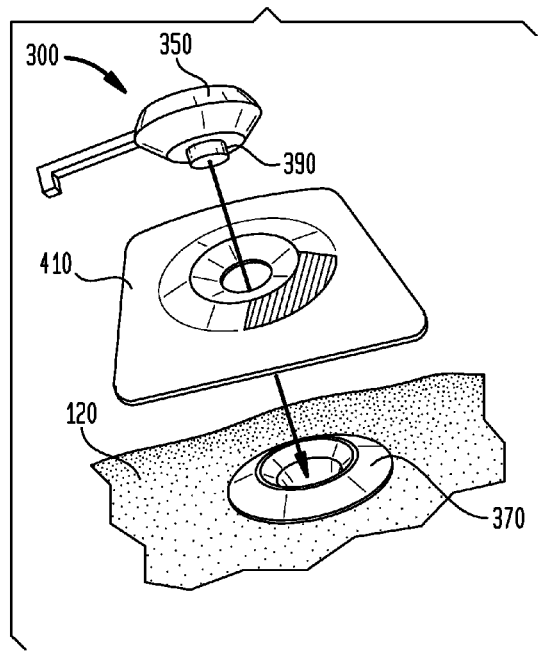
FIG. 3A is a perspective view of a wireless energy transfer system having an adhesive layer for securing the external charger to the implant device, according to an embodiment of the disclosure.
Figure 3B:
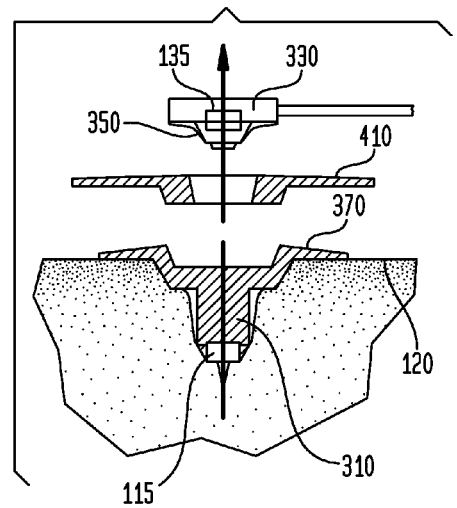
FIG. 3B is a cross-sectional view of the system of FIG. 3A.

Referring now to FIGS. 3A-3B, a wireless energy transfer system 300 is illustrated according to another embodiment of the disclosure. The system 300 includes an implant device 310 and an external charger 330. The implant device 310 has a feature 370 protruding across the skin 120. The external charger 330 includes a mating member 390. The system 300 further includes an adhesive layer 410. The adhesive layer 410 is configured to adhere to the feature 370 and a portion of the surrounding skin, on one hand, and to the at least some portions of the housing 350 of external charger 330, on the other hand. The adhesive layer 410 ensures that the external charger 330 is securely, yet releasably, aligned with the feature 370. Thus, the energy receiving element 115 may be aligned with the energy transmitting element 135 so as to facilitate wireless energy transmission therebetween.

The housings 150, 250, 350 of the external chargers 130, 230, 330 respectively, and the housings 140, 240, 340 of the implant devices 110, 210, 310 are configured to ensure proper alignment between the energy transmitting element 135 and the energy receiving element 115. In an exemplary embodiment, each of the housings 150, 250, 350 and the housings 140, 240, 340 may include magnets to assist and ensure proper alignment between the housings. In another embodiment, one of the housings 150, 250, 350 may include a latching mechanism and the other of the housings 140, 240, 340 may include a corresponding receiver to receive and secure the latching mechanism, or vice versa, thereby securing the housings in a desired alignment relative to one another. In yet other embodiment, the housings 150, 250, 350 and the housings 140, 240, 340 may include a bayonet-nut type connector or coupling therebetween to align and secure the housings to one another in a desired configuration. It will, thus, be understood that various alternatives may be employed to mechanically align and secure the housings 150, 250, 350 to the corresponding housings 140, 240, 340 without departing from the scope of the disclosure.

In an embodiment of the disclosure, the external chargers 130, 230, 330 as well as the implant devices 110, 210, 310 may be configured for telemetric data communication therebetween. For instance, one of the housings 140, 240, 340 of the implant devices 110, 210, 310 or the housings 150, 250, 350 of the external chargers 130, 230, 330 may include a sensor to detect whether the housings 150, 250, 350 are mated appropriately with the corresponding housings 140, 240, 340. The other of the housings 140, 150, 350 of the implant devices 110, 210, 310 or the housings 150, 250, 350 of the external chargers 130, 230, 330 may include a receiver to receive a signal generated by the sensor. Still further, the external chargers 130, 230, 330 as well as the implant devices 110, 210, 310 may be configured for one-way or two-way data communication therebetween. For instance, the implant devices 110, 210, 310 may include a processor and a transmitter for generating and transmitting a signal indicative of a state of the power-consuming device and the external chargers 130, 230, 330 may include a processor and a receiver for receiving the signal. Thus, while the energy may be transmitted wirelessly between the external charger and the implant device, there may be wireless or wired data communicate between the two without departing from the scope of the disclosure.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

DIFFERENT EMBODIMENTS

An implant device comprises a housing; and an energy receiving element disposed in the housing and configured to be electrically connected to an energy-consuming device. The implant device is configured to be mounted within a body of an animal. The housing comprises a feature configured to be accessible through skin of the animal and to receive a corresponding mating member of an external charger comprising an energy transmitting element. The energy receiving element is configured to receive energy wirelessly from the energy transmitting element when the external charger is mated with the housing.

In the implant device, the energy receiving element comprises a first coil and the energy transmitting element comprises a second coil; and wherein the first and second coils are configured to transmit energy inductively therebetween.

In the implant device, the feature of the housing protrudes through the skin of the animal.

In the implant device, the feature of the housing comprises an indentation; and the corresponding mating member comprises a button configured to mate with the indentation.

In the implant device, the energy receiving element comprises an RF antenna.

In the implant device, the energy receiving element comprises an ultrasonic receiver.

In the implant device, the energy receiving element comprises an optical receiver.

In the implant device, the housing is configured to releasably secure the external charger therewith.

In the implant device, the housing comprises a layer of adhesive to releasably secure the external charger to the housing.

The implant device further comprises the energy consuming device disposed in the housing.

A wireless energy transfer system comprises an implant device configured to be at least partially mounted within a body of an animal. The implant device comprises a first housing; and an energy receiving element disposed in the first housing and configured to be electrically connected to an energy-consuming device. The first housing comprises a feature configured to be accessible through skin of the animal. The system further comprises an external charging device comprises a second housing; and an energy transmitting element disposed in the second housing and configured to be electrically connected to an energy source. The second housing comprises a mating member configured to mate with the feature of the first housing. When the first and second housings are mated to one another, the energy transmitting element is aligned to wirelessly transmit energy to the energy receiving element.

The system further comprises the energy consuming device arranged in the first housing and electrically connected to the energy receiving element.

The system further comprises means for securing the first housing to the second housing when the mating member is mated with the feature of the first housing.

In the system, the means comprises an adhesive layer configured to secure the first housing to the second housing.

In the system, the means comprises a first magnet disposed in the first housing and a second magnet in the second housing.

In the system, the means comprises a bayonet nut connector for securing the first housing and the second housing to one another.

In the system, the means comprises a latching mechanism for securing the first housing and the second housing to one another.

In the system, the first housing and the second housing are configured for telemetric data communication therebetween.

The invention claimed is:

1. A wireless energy transfer system comprising:
   an implant device including a housing and an energy receiving element disposed in the housing; and
   an external charger including an energy transmitting element and a mating member, the mating member defining a protrusion extending therefrom, the external charger and the housing defining a common axis extending therethrough when the external charger is received by the housing,
   wherein the implant device is configured to be mounted within a body of an animal,
   wherein the housing comprises a feature having a plurality of sidewalls defining an indentation therebetween, the feature being configured to extend from within the body of the animal to outside the body of the animal through an opening in a skin of the animal and the indentation being configured to physically receive and mechanically align with the protrusion extending from the corresponding mating member of the external charger, and
   wherein the energy receiving element is configured to be disposed in a parallel orientation along the common axis with the energy transmitting element, and the energy receiving element being configured to receive energy wirelessly from the energy transmitting element when the external charger is physically-mated with the housing.

2. The implant device of claim 1, wherein the housing is configured to releasably secure the external charger therewith.

3. The implant device of claim 2, wherein the housing comprises a layer of adhesive to releasably secure the external charger to the housing.

4. The implant device of claim 1, wherein the energy receiving element comprises a first coil and the energy transmitting element comprises a second coil, wherein the first and second coils are configured to transmit energy inductively therebetween.

5. The implant device of claim 1, wherein the feature of the housing protrudes through the skin of the animal.

6. The implant device of claim 1, wherein the mating member comprises a button configured to mate with the indentation.

7. The implant device of claim 1, wherein the energy receiving element comprises an RF antenna.

8. The implant device of claim 1, wherein the energy receiving element comprises an ultrasonic receiver.

9. The implant device of claim 1, wherein the energy receiving element comprises an optical receiver.

10. The implant device of claim 1, further comprising the energy consuming device disposed in the housing.

11. A wireless energy transfer system comprising:
    an implant device configured to be at least partially mounted within a body of an animal, the implant device comprising a first housing; and an energy receiving element disposed in the first housing, wherein the first housing comprises a feature having a plurality of sidewalls defining an indentation therebetween, the feature being configured to extend from within the body of the animal to outside the body of the animal through an opening in a skin of the animal, wherein the system further comprises:
- an external charging device comprising a second housing, the first housing and the second housing defining a common axis extending therethrough; and
- an energy transmitting element disposed in the second housing and configured to be electrically connected to an energy source, wherein the second housing comprises a mating member defining a protrusion extending therefrom, the protrusion being configured to physically insert within the indentation and mechanically align the mating member with the feature of the first housing, and wherein, when the first and second housings are mated to one another, the energy transmitting element is aligned in a parallel orientation along the common axis with the energy receiving element to wirelessly transmit energy to the energy receiving element.

12. The wireless energy transfer system of claim 11, further comprising means for securing the first housing to the second housing when the mating member is mated with the feature of the first housing.

13. The wireless energy transfer system of claim 12, wherein the means comprises an adhesive layer configured to secure the first housing to the second housing.

14. The wireless energy transfer system of claim 12, wherein the means comprises a first magnet disposed in the first housing and a second magnet in the second housing.

15. The wireless energy transfer system of claim 12, wherein the means comprises a bayonet nut connector for securing the first housing and the second housing to one another.

16. The wireless energy transfer system of claim 12, wherein the means comprises a latching mechanism for securing the first housing and the second housing to one another.

17. The wireless energy transfer system of claim 11, further comprising the energy consuming device arranged in the first housing and electrically connected to the energy receiving element.

18. The wireless energy transfer system of claim 11, wherein the first housing and the second housing are configured for telemetric data communication therebetween.

* * * * *